US007262013B2

(12) United States Patent
Boyd et al.

(10) Patent No.: US 7,262,013 B2
(45) Date of Patent: Aug. 28, 2007

(54) BISULFITE METHOD

(75) Inventors: Victoria L. Boyd, San Carlos, CA (US); Gerald Zon, San Carlos, CA (US)

(73) Assignee: Applera Corporation, Foster City, CA (US)

( * ) Notice: Subject to any disclaimer, the term of this patent is extended or adjusted under 35 U.S.C. 154(b) by 313 days.

(21) Appl. No.: 10/926,534

(22) Filed: Aug. 26, 2004

(65) Prior Publication Data

US 2005/0079527 A1 Apr. 14, 2005

Related U.S. Application Data

(60) Provisional application No. 60/520,941, filed on Nov. 17, 2003, provisional application No. 60/498,996, filed on Aug. 29, 2003.

(51) Int. Cl.
*C12Q 1/68* (2006.01)
*C07H 21/02* (2006.01)
*C07H 21/04* (2006.01)

(52) U.S. Cl. .................... 435/6; 536/23.1; 536/24.3
(58) Field of Classification Search .................. 435/6; 536/22.1, 23.2, 24.3, 23.1
See application file for complete search history.

(56) References Cited

U.S. PATENT DOCUMENTS

| | | | |
|---|---|---|---|
| 6,214,556 B1 | 4/2001 | Olek et al. | |
| 6,251,594 B1 | 6/2001 | Gonzalgo et al. | |
| 6,331,393 B1 | 12/2001 | Laird et al. | |
| 6,511,810 B2 | 1/2003 | Bi et al. | |
| 2004/0152080 A1 | 8/2004 | Berlin et al. | |
| 2005/0095623 A1 | 5/2005 | Zon et al. | |

FOREIGN PATENT DOCUMENTS

| | | |
|---|---|---|
| EP | 1394173 A1 | 3/2004 |
| JP | 1995/265082 A | 10/1995 |
| WO | WO02/30944 | 4/2002 |
| WO | WO 02/31186 A | 4/2002 |
| WO | WO03/031649 A2 | 4/2003 |
| WO | WO 2004/067545 A | 8/2004 |
| WO | WO 05/021563 A | 3/2005 |

OTHER PUBLICATIONS

U.S. Appl. No. 60/499,113, filed Aug. 29, 2003, Zon.
U.S. Appl. No. 60/520,942, filed Nov. 17, 2003, Zon.
U.S. Appl. No. 60/499,106, filed Aug. 29, 2003, Zon.
U.S. Appl. No. 60/523,054, filed Nov. 17, 2003, Zon.
U.S. Appl. No. 60/499,082, filed Aug. 29, 2003, Zon.
U.S. Appl. No. 60/523,056, filed Nov. 17, 2003, Zon.
U.S. Appl. No. 60/498,996, filed Aug. 29, 2003, Zon.
U.S. Appl. No. 60/520,941, filed Nov. 17, 2003, Zon.
Shapiro and Klein, "Reactions of Cytosine Derivatives With Acidic Buffer Solutions", Biochemistry, vol. 6, No. 11, Nov. 1967, pp. 3576-3582.
Shapiro et al., "Reactions of Uracil and Cytosine Derivatives With Sodium Bisulfite. A Specific Deamination Method", Journal of the American Chemical Society/92:2/Jan. 28, 1970.
Hayatsu et al., "Reaction of Sodium Bisulfite With Uracil, Cytosine, and Their Derivatives", Biochemistry, vol. 9, No. 14, 1970, pp. 2858-2865.
Shapiro and Weisgras, "Bisulfite-Catalyzed Transamination of Cytosine and Cytidine", Biochemical and Biophysical Research Communications, vol. 40, No. 4, 1970, pp. 839-843.
Shapiro et al., "Nucleic Acid Reactivity and Conformation", The Journal of Biological Chemistry, vol. 248, No. 11, Issue of Jun. 10, pp. 4060-4064, 1973.
Shapiro et al., "Deamination of Cytosine Derivatives by Bisulfite. Mechanism of the Reaction", Journal of the American Chemical Society/96:3/Feb. 6, 1974.
Hikoya Hayatsu, "Bisulfite Modification of Nucleic Acids and Their Constituents", Prog Nucleic Acid Res Mol Biol, 1976, 16 75-124.
Wang et al., "Comparison of Bisulfite Modification of 5-Methyldeoxycytidine and Deoxycytidine Residues" Nucleic Acids Research, vol. 8, No. 20, 1989, pp. 4776-4790.
Miller and Cushman, "Selective Modification of Cytosines in Oligodeoxyribonucleotides", Bioconjugate Chem 1992, 3, 74-79.
Frommer et al., "A Genomic Sequencing Protocol That Yields a Positive Display of 5-Methylcytosine Residues in Individual DNA Strands", Proc. Natl. Acad. Sci. USA, vol. 89, pp. 1827-1831, Mar. 1992, Genetics.
Kumar et al., "Immunoaffinity Chromatography to Isolate Methylated DNA Using Immobilized Anti-5 Methyl Cytosine Antibody", Biotechnology Techniques, vol. 5, No. 6, 469-470 (1991).
Molander et al., "Bisulfite Ion-Catalyzed Transamination of Cytosine Residues With a, w-Alkanediamines: The Effect of Chain Length on the Reaction Kinetics", Bioconjugate Chem. 1993, 4, 362-365.
Clark et al., "High Sensitivity Mapping of methylated Cytosines", 2990-2997, Nucleic Acids Research, 1994, vol. 22, No. 15.
Paul and Clark, "Cytosine Methylation: Quantitation by Automated Genomic Sequencing and GENESCAN™ Analysis", BioTechniques 21:126-133 (Jul. 1996).
Olek et al., "A Modified and Improved Method for Bisulphite Based Cytosine Methylation Analysis", 5064-5066, Nucleic Acids Research, 1996, vol. 24, No. 24.
Herman et al., "Methylation-specific PCR: A Novel PCR Assay for Methylation Status of CpG Islands", Proc. Natl. Acad. Sci. USA, vol. 93, pp. 9821-9826, Sep. 1996, Medical Sciences.
Rein et al., "Active Mammalian Replication Origins Are Associated With a High-Density Cluster of $^m$CpG Dinulceotides", Molecular and Cellular Biology, Jan. 1997, vol. 17, No. 1, p. 416-426.
Paulin et al., "Urea Improves Efficiency of Bisulphite-Mediated Sequencing of 5'-Methylcytosine in Genomic DNA", Nucleic Acids Research, 1998, vol. 26, No. 21, 5009-5010.
Warnecke et al., "Bisulfite Sequencing in Preimplantation Embryos: DNA Methylation Profile of the Upstream Region of the Mouse Imprinted H19 Gene", Genomics 51, 182-190 (1990), Article No. GE985371.
Oakeley, E., et al., "Quantification of 5-Methylcytosine in DNA by the Chloroacetaldehyde Reaction", BioTechniques 27:744-752 (Oct. 1999).

(Continued)

*Primary Examiner*—Ethan Whisenant
(74) *Attorney, Agent, or Firm*—Michael A. Patane; Shirley A. Recipon

(57) ABSTRACT

The invention provides methods for purifying bisulfite-treated nucleic acid samples.

15 Claims, No Drawings

OTHER PUBLICATIONS

Oakeley, "DNA Methylation Analysis: A Review of Current Methodologies", Pharmacology & Therapeutics 84 (1999) 389-400.

Thomassin et al., "Identification of 5-Methylcytosine in Complex Genomes", Methods, 19, 465-475 (1999).

Grunau et al., "Bisulfite Genomic Sequencing: Systematic Investigation of Critical Experimental Parameters", Nucleic Acids Research, 2001, vol. 29, No. 13, e65.

Kerjean et al., "Bisulfite Genomic Sequencing of Microdissected Cells", Nucleic Acids Research, 2001, vol. 29, No. 21 e106.

Trinh et al., "DNA Methylation Analysis by MethyLight Technology", Methods 25, 456-462 (2001).

Balog et al., "Parallel Assessment of CpG Methylation by Two-Color Hybridization With Oligonucleotide Arrays", Analytical Biochemistry, 309 (2002) 301-310.

Rand et al., "Conversion-Specific Detection of DNA Methylation using Real-Time Polymerase Chain Reaction (ConLight-MSP) to Avoid False Positives", Methods, 27 (2002), 114-120.

Frigola et al., "Methylome Profiling of Cancer Cells by Amplification of Inter-Methylated Sites (AIMS)", Nucleic Acids Research, 2002, vol. 30, No. 7 e28.

Fraga and Esteller, "DNA Methylation: A Profile of Methods and Applications", BioTechniques 33:632-649 (Sep. 2002).

El-Maarri et al., "A Rapid, Quantitative, Non-Radioactive Bisulfite-SNuPE-IP RP HPLC Assay for Methylation Analysis at Specific CpG Sites", Nucleic Acids Research, 2002, vol. 30, No. 6, e25.

Li and Dahiya, "MethPrimer: Designing Primers for Methylation PCRs", Bioinformatics, vol. 18, No. 11, 2002, pp. 1427-1431.

Okamoto et al., "Site-Specific Discrimination of Cytosine and 5-Methylcytosine in Duplex DNA by Peptide Nucleic Acids", JACS Communications (Apr. 10, 2002).

Friso et al., "A Method to Assess Genomic DNA Methylation Using High-Performance Liquid Chromatography/Electrospray Ionization Mass Spectrometry", Anal. Chem. 2002, 74, 4526-4531.

Mills and Ramsahoye, "DNA Methylation Protocols", Methods in Molecular Biology, vol. 200, (2002).

Ushijima et al., "Fidelity of the Methylation Pattern and its Variation in the Genome", Genome Research, (2003), pp. 868-874.

"EZ DNA Methylation Kit™", Instructions, Zymo Research.

Humeny, A.., et al., Detection and analysis of enzymatic DNA methylation of oligonucleotide substrates by matrix-assisted laser desorption ionization time-of-flight mass spectrometry, Anal. Biochem. 313 (2003) 160-166.

Kinoshita, H., et al., Screening hypermethylated regions by methylation-sensitive single-strand conformational polymorphism, Anal. Biochem. 278 (2000) 165-169.

Kubareva et al., "Determination of Methylation Site of DNA-Methyl-Transferase Nylax by a Hybrid Method," Biotechniques, Eaton Publishing, Natick, U.S., vol. 33, No. 3, Sep. 2002, pp. 526-531.

Boyd, et al., Bisulfite conversation of genomic DNA for methylation analysis: protocol simplification with higher recovery applicable to limited samples and increased throughput, Analytical Biochemistry, Academic Press, San Diego, CA, U.S., vol. 326, No. 2, Mar. 15, 2004, pp. 278-280.

Komiyama, et al., "Catalysis of diethylenetriamine for bisulfite-induced deamination of cytosine in oligodeoxyribonucleotides," *Tetrahedron Letters* (1994) 35(44): 8185-8188.

International Search Report mailed Jan. 31, 2005 from International Application No. PCT/US2004/028089, published as WO/2005/021803.

International Search Report mailed May 18, 2005 from International Application No. PCT/US04/28070, published as WO/2005/021778.

International Search Report mailed Apr. 15, 2005 from International Application No. PCT/US04/27992, published as WO/2005/021563.

International Search Report mailed Jun. 27, 2005 from International Application No. PCT/US2004/028032, published as WO/2005/021802.

"EZ DNA Methylation Kit™", Instructions, Zymo Research, Mar. 11, 2003.

SEQUENCE LISTING

<160> NUMBER OF SEQ ID NOS: 20

<210> SEQ ID NO 1
<211> LENGTH: 24
<212> TYPE: DNA
<213> ORGANISM: Artificial Sequence
<220> FEATURE:
<223> OTHER INFORMATION: Sense

<400> SEQUENCE: 1
ttattagagg gtggggtgga ttgt                                   24

<210> SEQ ID NO 2
<211> LENGTH: 22
<212> TYPE: DNA
<213> ORGANISM: Artificial Sequence
<220> FEATURE:
<223> OTHER INFORMATION: Antisense

<400> SEQUENCE: 2
caaccccaaa ccacaaccat aa                                     22

<210> SEQ ID NO 3
<211> LENGTH: 24
<212> TYPE: DNA
<213> ORGANISM: Artificial Sequence
<220> FEATURE:
<223> OTHER INFORMATION: Sense

<400> SEQUENCE: 3
ttattagagg gtggggcgga tcgc                                   24

<210> SEQ ID NO 4
<211> LENGTH: 21
<212> TYPE: DNA
<213> ORGANISM: Artificial Sequence
<220> FEATURE:
<223> OTHER INFORMATION: Antisense

<400> SEQUENCE: 4
gaccccgaac cgcgaccgta a                                    21

<210> SEQ ID NO 5
<211> LENGTH: 29
<212> TYPE: DNA
<213> ORGANISM: Artificial Sequence
<220> FEATURE:
<223> OTHER INFORMATION: Sense

<400> SEQUENCE: 5
tttgtgtttt gatgtttgta ggtttttgt                            29

<210> SEQ ID NO 6
<211> LENGTH: 28
<212> TYPE: DNA
<213> ORGANISM: Artificial Sequence
<220> FEATURE:
<223> OTHER INFORMATION: Antisense

<400> SEQUENCE: 6
aactccacac tcttccaaaa acaaaaca                             28

<210> SEQ ID NO 7
<211> LENGTH: 23
<212> TYPE: DNA
<213> ORGANISM: Artificial Sequence
<220> FEATURE:
<223> OTHER INFORMATION: Sense

<400> SEQUENCE: 7
tttcgacgtt cgtaggtttt cgc                                  23

<210> SEQ ID NO 8
<211> LENGTH: 22
<212> TYPE: DNA
<213> ORGANISM: Artificial Sequence
<220> FEATURE:
<223> OTHER INFORMATION: Antisense

<400> SEQUENCE: 8
gcactcttcc gaaaacgaaa cg                                   22

<210> SEQ ID NO 9
<211> LENGTH: 27
<212> TYPE: DNA
<213> ORGANISM: Artificial Sequence
<220> FEATURE:
<223> OTHER INFORMATION: Sense

<400> SEQUENCE: 9
ggaggatagt tggattgagt taatgtt                              27

<210> SEQ ID NO 10
<211> LENGTH: 20
<212> TYPE: DNA
<213> ORGANISM: Artificial Sequence
<220> FEATURE:
<223> OTHER INFORMATION: Antisense

<400> SEQUENCE: 10
caatccctcc caaacaccaa                                      20

<210> SEQ ID NO 11
<211> LENGTH: 24
<212> TYPE: DNA
<213> ORGANISM: Artificial Sequence -continued

```
<220> FEATURE:
<223> OTHER INFORMATION: Sense

<400> SEQUENCE: 11
ggatagtcgg atcgagttaa cgtc                                              24

<210> SEQ ID NO 12
<211> LENGTH: 15
<212> TYPE: DNA
<213> ORGANISM: Artificial Sequence
<220> FEATURE:
<223> OTHER INFORMATION: Antisense

<400> SEQUENCE: 12
ccctcccaaa cgccg                                                        15

<210> SEQ ID NO 13
<211> LENGTH: 29
<212> TYPE: DNA
<213> ORGANISM: Artificial Sequence
<220> FEATURE:
<223> OTHER INFORMATION: Sense

<400> SEQUENCE: 13
ttttgatgta gatgttttat tagggttgt                                         29

<210> SEQ ID NO 14
<211> LENGTH: 24
<212> TYPE: DNA
<213> ORGANISM: Artificial Sequence
<220> FEATURE:
<223> OTHER INFORMATION: Antisense

<400> SEQUENCE: 14
accacctcat cataactacc caca                                              24

<210> SEQ ID NO 15
<211> LENGTH: 24
<212> TYPE: DNA
<213> ORGANISM: Artificial Sequence
<220> FEATURE:
<223> OTHER INFORMATION: Sense

<400> SEQUENCE: 15
acgtagacgt tttattaggg tcgc                                              24

<210> SEQ ID NO 16
<211> LENGTH: 20
<212> TYPE: DNA
<213> ORGANISM: Artificial Sequence
<220> FEATURE:
<223> OTHER INFORMATION: Antisense

<400> SEQUENCE: 16
cctcatcgta actacccgcg                                                   20

<210> SEQ ID NO 17
<211> LENGTH: 25
<212> TYPE: DNA
<213> ORGANISM: Artificial Sequence
<220> FEATURE:
<223> OTHER INFORMATION: Sense

<400> SEQUENCE: 17
tgtgatgtgt ttgtattttg tggtt                                             25
```

```
-continued

<210> SEQ ID NO 18
<211> LENGTH: 23
<212> TYPE: DNA
<213> ORGANISM: Artificial Sequence
<220> FEATURE:
<223> OTHER INFORMATION: Antisense

<400> SEQUENCE: 18
ccatacaata accaaacaac caa                                              23

<210> SEQ ID NO 19
<211> LENGTH: 19
<212> TYPE: DNA
<213> ORGANISM: Artificial Sequence
<220> FEATURE:
<223> OTHER INFORMATION: Sense

<400> SEQUENCE: 19
gcgttcgtat tttgcggtt                                                   19

<210> SEQ ID NO 20
<211> LENGTH: 22
<212> TYPE: DNA
<213> ORGANISM: Artificial Sequence
<220> FEATURE:
<223> OTHER INFORMATION: Antisense

<400> SEQUENCE: 20
cgtacaataa ccgaacgacc ga                                               22
```

BISULFITE METHOD

This applications claims benefit of priority to U.S. Provisional Application Ser. Nos. 60/498,996 filed Aug. 29, 2003 and 60/520,941 filed Nov. 17, 2003, each of which is incorporated by reference.

FIELD

The invention relates generally to methods for purifying bisulfite-treated nucleic acid samples.

BACKGROUND

Assessment of methylation of DNA is useful in many research, diagnostic, medical, forensic, and industrial fields. Key to this assessment is converting cytosine to uracil, but not methylcytosine to thymine. One basic method for such conversion, employing sodium bisulfite, is well known. Over the years, the method has been improved in attempts to overcome disadvantages that include tedious procedures, lengthy reaction times, and DNA degradation. The currently most commonly used protocol is taught by J. Herman, *Proc. Natl. Acad. Sci.* 93, 9821–26 (1996), incorporated herein by reference in its entirety. This method involves denaturation, reaction with sodium bisulfite in the presence of hydroquinone, and subsequent completion of the modification by treatment with NaOH. Despite the attempts to improve the protocol, current procedures still require pre-denaturation of the genomic DNA (gDNA) to single stranded DNA (ssDNA), preparation fresh solutions of sodium bisulfite (NaHSO$_3$), typically about 3M, and inclusion an anti-oxidant (e.g., hydroquinone). The protocol also involves long reaction times and tedious clean-up procedures.

In addition, the currently employed sodium bisulfite protocols are plagued by reports of incomplete conversion, irreproducible results, and other problems. In some cases, the reaction results in significant DNA degradation (reportedly as high as 96%), making it difficult to obtain enough sample for further analysis. See. S. J. Clark et al. *Nucleic Acid Research* 2001, 29 no. 13, 65.

It has been discovered that bisulfite methods that employ magnesium bisulfite, polyamine compounds, and/or quaternary amine compounds provide useful alternatives to sodium bisulfite conversion reactions. These discoveries are the subjects of co-owned applications entitled "Method And Materials For Polyamine Catalyzed Bisulfite Conversion Of Cytosine To Uracil" (U.S. application Ser. No. 60/499,113 filed Aug. 29, 2003, and also application Ser. No. 60/520,942 having the same title and filed Nov. 17, 2003), "Method And Materials For Quaternary Amine Catalyzed Bisulfite Conversion Of Cytosine To Uracil" (U.S. application Ser. No. 60/499,106 filed Aug. 29, 2003, and also application Ser. No. 60/523,054 having the same title and filed Nov. 17, 2003), and "Method and Materials for Bisulfite Conversion of Cytosine to Uracil (U.S. application Ser. No. 60/499,082 filed Aug. 29, 2003, and also application Ser. No. 60/523, 056 (5180P2) having the same title and filed Nov. 17, 2003), all of which are hereby incorporated by reference in their entirety.

Two widely reported methods of purification used in connection with bisulfite conversion reactions utilize either adsorbtive resins, such as the Promega Wizard resin or similar DNA binding resins, or dialysis. Given the importance of assessment of DNA methylation, it can be seen that there is a need for improved methodology for conversion of cytosine to uracil, and for the purification of the products of such conversion. Applicants have discovered such an improved methodology which is the subject of the co-owned application entitled: "Improved Bisulfite Method" (U.S. application Ser. No. 60/498,996 filed Aug. 29, 2003, and also application Ser. No. 60/520,941 having the same title and filed Nov. 17, 2003), all of which are hereby incorporated by reference in its their entirety.

SUMMARY

In certain embodiments the invention provides methods of purifying bisulfite-treated nucleic acid samples.

In some embodiments, the present invention provides methods for preparing a sample, comprising the steps of providing a nucleic acid comprising at least one cytosine nucleobase; contacting the sample with a bisulfite conversion reagent; and purifying the contacted sample using a size-exclusion device. In some embodiments, the purifying step comprises contacting the sample with a base to increase the pH and facilitate completion of the conversion to uracil. In some embodiments, the base is NaOH, for example at about 1M concentration.

In some embodiments, the size-exclusion device can have a cutoff of 300K, or 100K, or 30K.

In some embodiments, the bisulfite conversion reagent includes sodium bisulfite. In further embodiments, the bisulfite conversion reagent includes magnesium bisulfite.

In further embodiments, the present invention provides methods of purifying a bisulfite-treated nucleic acid sample, comprising the steps of treating the sample with a base; and washing the treated sample; wherein at least one of the treating step and the washing step is performed using a size-exclusion device. In some embodiments, the treating step and the washing step are performed using a size-exclusion device. In some embodiments, the base is NaOH, for example at about 0.1M concentration. In some embodiments, the size-exclusion device can have a cutoff of 100K, or 30K, and possibly as high as 300K.

In some embodiments, the bisulfite treatment comprises reaction with sodium bisulfite. In further embodiments, the bisulfite treatment comprises reaction with magnesium bisulfite or manganese bisulfite, e.g., at a concentration of from about 0.5 M to about 2.5 M, or from about 1 M to about 2 M.

In some embodiments, methods are provided for the purification of a bisulfite-treated nucleic acid comprising the steps of:
(a) placing a bisulfite-treated nucleic acid sample in a size-exclusion device;
(b) optionally washing said sample in said size-exclusion device;
(c) treating said washed sample with a base in said size-exclusion device; and
(d) optionally washing said sample.

In some embodiments, step (d) is performed in said size exclusion device.

In further embodiments, the methods further comprise the step of extracting said sample with a buffer, which in some embodiments is TE buffer. In some such embodiments, the solubilization with the buffer is performed in the size exclusion device.

In some embodiments, the base is NaOH, for example at about 0.1M concentration. In some embodiments, the size-exclusion device can have a cutoff of 300K, or 100K, or 30K. In some embodiments, the methods further comprise repeating one of more of said step (b) and said step (d).

In some embodiments, one or more steps of the methods that are performed in the size exclusion device are performed using centrifugation, for example at about 2800 RPM (500×g in a model 5414 Eppendorf centrifuge). In some embodiments, the centrifugations are performed for about 8 minutes. In some embodiments, the size exclusion device is subjected to positive pressure (e.g., gaseous pressure) that is applied above the reaction mixture to push solvent and low molecular weight species through the device, with or without centrifugation.

In some embodiments of each of the foregoing methods, the nucleic acid, bisulfite-treated nucleic acid, or nucleic acid sample contains about 0.3 to about 300 ng DNA. In other embodiments, more DNA is contained in the sample. In certain embodiments, each of the washing steps used 200–350 µL of the respective wash solution.

Following desulfonation of the bisulfite-treated nucleic acid(s), the obtained product may be used in any of a wide variety of analytical or preparative procedures, such as amplification (e.g., by PCR, whole genome amplification, etc.), sequencing (which may optionally follow amplification), differential hybridization, mass spectrometry, or other techniques (e.g., see A. Humeny et al., Detection and analysis of enzymatic DNA methylation of oligonucleotide substrates by matrix-assisted laser desorption ionization time-of-flight mass spectrometry, Anal. Biochem. 313 (2003) 160–166; R. P. Balog et al., Parallel assessment of CpG methylation by two-color hybridization with oligonucleotide arrays, Anal. Biochem. 309 (2002) 301–310; H. Kinoshita et al., Screening hypermethylated regions by methylation-sensitive single-strand conformational polymorphism, Anal. Biochem. 278 (2000) 165–169; E. J. Oakeley et al., DNA methylation analysis: a review of current methodologies, Pharmacology and Therapeutics 84 (1999) 389–400; and C. Granau et al., Bisulfite genomic sequencing: systematic investigation of critical experimental parameters, Nucleic Acids Res. 29 (2001) e65.

In some embodiments, the methylation status of one or more cytosines in the target nucleic acid(s) can be determined by any suitable method. Typically, methylation status can be determined by measuring the presence or relative amount of uracil at a nucleotide position that was previously non-methylated cytosine, and was converted to uracil by the bisulfite treatment. If desired, the presence or relative amount of residual cytosine at the same nucleotide position (indicating the presence of methylcytosine) can be measured for comparison with the amount of uracil, to determine the degree of methylation at the particular nucleotide position. Appropriate control experiments can also be performed to correct for incomplete transformation of cytosine to uracil, if desired.

The presence or amount of uracil and/or methylcytosine at a particular nucleotide position can be measured by any suitable method, such as DNA sequencing (e.g., by the Sanger method or Maxam-Gilbert method or subsequent embodiments thereof (e.g., using dye-labeled terminators or dye-labeled primers, such as discussed in WO 02/30944 and by Ansorge et al. DNA Sequencing Strategies—Automated and Advanced Approaches, John Wiley & Sons, New York, 1997)), PCR (e.g., primer-specific PCR), oligonucleotide ligation assay (OLA) or other ligation-dependent techniques (e.g., see U.S. Pat. No. 6,511,810 and references cited therein), single base extension (over the potential methylation site), mass spectrometry, real time PCR (e.g., using labeled probes that are complementary to C and or U), microarrays comprising sequence specific probes, etc. Various exemplary techniques are also described by Kirk et al., Nucl. Acids Res., 30:3295–3311 (2002).

DETAILED DESCRIPTION

It is to be understood that both the foregoing general description and the following detailed description are exemplary and explanatory only and are not restrictive of the invention. In this application, the use of the singular includes the plural unless specifically stated otherwise. In this application, the use of "or" means "and/or" unless stated otherwise. Furthermore, the use of the term "including", as well as other forms, such as "includes" and "included", is not intended to be limiting. Also, terms such as "element" or "component" encompass both elements and components comprising one unit and elements and components that comprise more than one subunit unless specifically stated otherwise.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Definitions

As used herein, the term "gDNA" refers to genomic DNA.

The term "PCR" is intended to denote polymerase chain reaction, as is well known in the art. The term "MSP" denotes methyl specific PCR such as described by J. Herman, Proc. Natl. Acad. Sci. 93, 9821–26 (1996), and modified as discussed herein.

The term "nucleic acid" includes, for example, nucleobase-containing polymeric compounds, including naturally occurring and non-naturally occurring forms thereof, for example and without limitation, genomic DNA, cDNA, hnRNA, mRNA, rRNA, tRNA, fragmented nucleic acids, nucleic acids obtained from subcellular organelles such as mitochondria or chloroplasts, and nucleic acids obtained from microorganisms or DNA or RNA viruses that may be present on or in a biological sample.

"Purification", as used herein, is a process of removing one or more contaminating species, for example and not limitation, excess salt (e.g. bisulfite), from a bisulfite-treated nucleic acid sample. Likewise, purified product or purified nucleic acid refer to the resultant products of such purification.

The term "size-exclusion device" refers to filtration devices capable of separating materials on the basis of their size. One non-limiting exemplary class of such devices is the filtration-type class, wherein sample components are separated on the basis of molecular weight through a matrix that allows small molecules to pass through more rapidly than larger molecules. Typically, filtration-type devices are characterized by a molecular weight cutoff that represents an upper limit of the molecular weight of molecules that are able to pass through the matrix. Typically, a sample solution or reaction mixture is forced through the molecular weight separation matrix by application of centrifugal force (by centrifugation) or positive pressure (e.g., application of gaseous pressure or application of a piston above the solution or reaction mixture). In some embodiments, the matrix is provided as a membrane. Such devices typically have an integral filter material between an upper and a lower chamber. Examples of such size-exclusion devices are the commercially available Microcon 300, 100, 50, 30, 3, and Centricon 3K, 30K, 50K, 100K, and 300K (all from Millipore), and Nanosep available in 10K, 30K, 100K and 300K cutoffs (all from Pall Corp.). The Microcon and Centricon units are the same devices, but differ in volume of solution that can be used. Also available is a 96-well plate, for processing many samples simultaneously. Use of such a multi-sample well plate renders the purification process less burdensome. Thus, in some embodiments, the "size-exclusion device" comprises a porous, size-discriminating barrier that allows smaller molecules (e.g., smaller than a predetermined molecular weight cutoff, as exemplified above) to pass through while retaining larger molecules (which have molecular weights greater than the cutoff). For example, such a device can be an ultrafiltration device, comprising a porous membrane, such as a Microcon or Centricon filtration device of the type just described.

In other embodiments, the "size exclusion device" may comprise size exclusion (gel filtration) particles, such as Sephadex, or even the Edge Biosystems Performa size exclusion device used in the sequencing reported herein, may also be used. Such embodiments operate by retaining smaller molecules which can be transiently trapped in pores of the particles while larger molecules pass through with bulk eluant, such that larger molecules elute first.

Bisulfite ion has its accustomed meaning of $HSO^-_3$. Typically, bisulfite is used as an aqueous solution of a bisulfite salt, for example magnesium bisulfite, which has the formula $Mg(HSO_3)_2$, or sodium bisulfite, which has the formula $NaHSO_3$.

ssDNA refers to single stranded DNA, resulting typically, but not always, from denaturing DNA.

TE buffer refers to a buffering solution of 10 mM TRIS-HCl and 1 mM EDTA is a standard solution used in nucleic acid analyses, and well-known in the art.

Unless otherwise specified, reference herein to "cytosine" refers to unmethylated cytosine and "conversion" refers to specific conversion of unmethylated cytosine to uracil, and methyl cytosine is not converted to thymine.

The term "bisulfite conversion reagent" is intended to denote a reagent used for the bisulfite conversion of cytosine to uracil. Examples of bisulfite conversion reagents include solutions of sodium bisulfite or magnesium bisulfite.

The term "bisulfite treated nucleic acid" is intended to mean a nucleic acid that has been contacted with bisulfite ion in an amount appropriate for bisulfite conversion protocols known in the art, or for those reported in the contemporaneously filed applications described herein. Thus, the term "bisulfite treated nucleic acid" includes nucleic acids that have been contacted with, for example, magnesium bisulfite or sodium bisulfite, prior to treatment with base.

Methods are also provided for the preparation or purification of bisulfite-treated nucleic acid samples using at least one separation based on size exclusion. Methods described herein can provide suitable PCR substrates even using ten to twenty fold less sample than typically reported when using known purification methods.

In some embodiments, the methods include providing a nucleic acid comprising at least one cytosine nucleobase; contacting said sample with a bisulfite conversion reagent; and purifying said contacted sample using a size-exclusion device. Contacting the nucleic acids sample with the bisulfite conversion reagent can be accomplished in any of the ways currently known for performing bisulfite conversion reactions, or by any of the methods disclosed in the contemporaneously filed applications described herein. See, for example, J. Herman, *Proc. Natl. Acad. Sci.* 93, 9821–26 (1996).

Also provided are methods of purifying or preparing a bisulfite-treated nucleic acid sample, that include the steps of treating the sample with a base; and washing the treated sample, where at least one of the treating step and the washing step is performed using a size-exclusion device. In accordance with some embodiments of the invention, both the treating step and the washing step can be performed in a size-exclusion device. In some such embodiments, the product of the reaction between a nucleic acid and a bisulfite-containing reagent is placed in a size exclusion device as described herein, and then treated in situ with a base solution (typically NaOH at about 0.1M) sufficient to complete the bisulfite conversion reaction (i.e., sufficient to desulfonate the sulfonate adduct of cytosine described above). The resulting desulfonated sample is then washed, optionally in situ in the size exclusion device.

In some embodiments, the methods further include the step of extracting the sample with a buffer, typically but not limited to TE buffer (e.g., Sambrook et al., Molecular Cloning—A Laboratory Manual, Second Ed., Cold Spring Harbor Press, 1989). The solubilization with buffer to recover the DNA also can be performed in situ, in the size exclusion device. The methods of the invention also can include a plurality of washing steps, which also can be performed in situ, in the size exclusion device. In some embodiments, the bisulfite treatment reaction is carried out in the device.

Thus, in some embodiments, methods of the invention can be performed in situ, in the size exclusion device, with centrifugation after one or more of the steps, for example at about 2800 RPM (500×g, as per manufacturer's advise) for about 8 minutes, and with subsequent removal of the filtrate. In one typical but non-limiting protocol, the nucleic acid sample is first diluted with water. Then, after centrifugation and separation, the sample is further washed with water 1–3 times with centrifugation and removal of the filtrate after each. The water wash is then followed by a 0.1N NaOH wash and centrifugation for about 6–8 minutes with separation of the filtrate. Another water wash follows, again with centrifugation and removal of the filtrate. Finally TE buffer, typically about pH 8, is added to the sample, which is then allowed to sit for about five minutes, after which the sample is collected, The sample can be collected either by removing the TE by pipette, or inverting the devise and collecting the contents by centrifugation.

The molecular weight cut-off of the size exclusion device is selected to retain desired components, and allow undesired species (e.g., bisulfite) to pass through. In some embodiments, the size-exclusion device has a 300K cut off, or a 100K cut off, or a 30K cut off. It will be appreciated, however, that size exclusion device having any suitable cut-off can be employed in the present methods.

It has been discovered in accordance with the present invention that an improvement in the recovery of the bisulfite converted DNA (cytosine to uracil) is seen, regardless of the bisulfite conversion reaction employed, by using the clean-up process described herein. Thus, the methods of the invention are amenable to the well-known and accepted sodium bisulfite conversion reaction to produce bisulfite-treated DNA for subsequent PCR and/or other processing. Other methods of converting cytosine to uracil also may be used, for example those methods described in the contemporaneously filed applications described above.

It also has been discovered in accordance with the present invention that the reported levels of nucleic acid degradation seen in bisulfite conversions do not occur during the conversion reaction as reported, but rather low yields are due to loss of material from the tedious clean-up process. Accordingly, the present invention provides simple and efficient clean-up processes that can reduce loss of the nucleic acid in the sample.

While not wishing to be bound by a particular theory, it is believed that the conversion of cytosine to uracil occurs in two separate, kinetically distinct steps, shown in Scheme I below:

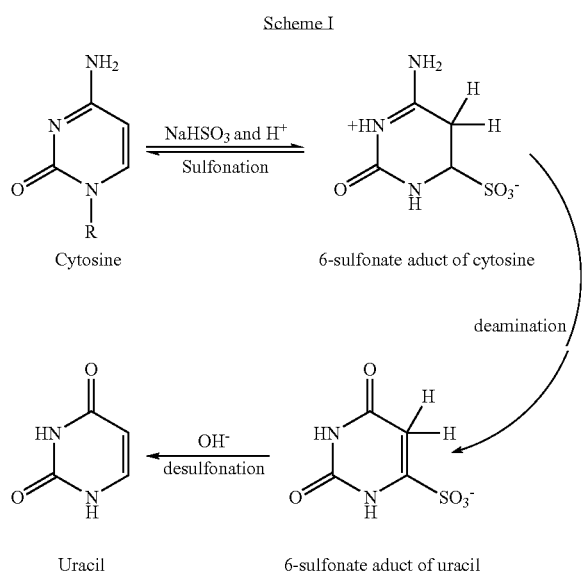

The first step is the addition of the —$SO_3$ moiety to the 6-position of the cytosine ring, and a hydrogen atom to the 5-position of the ring, to form a sulfonate adduct. The resulting adduct exists in equilibrium with the unmodified cytosine, and is favored at both low reaction temperatures, and at low pH (where pH 5 is usually stated as optimal). A low pH is, therefore, necessary to the overall conversion of cytosine to uracil. The second step of the conversion is deamination. It has been reported that the velocity of the deamination reaction is first order as the concentration of the 6-sulfonate-adduct of uracil forms. See Hayatsu, *Prog. Nucleic Acid Res. Mol. Biol.* 1976 16, 75–124, incorporated herein by reference in its entirety. As desulfonation of uracil-6-sulfonate is not facile under the acidic reaction conditions, a treatment with base at pH 10 or higher is usually needed to desulfonate the uracil prior to PCR or other processing.

Without wishing to be bound by any particular theory, one possible basis for the success of the presently disclosed methods is the difference in the solubility of the bisulfite-converted DNA and the gDNA. The gDNA, after conversion, is a single stranded DNA and, initially, is believed to be sulfonated at the 6-C position of the newly formed uracil ring, as seen in Scheme 1 above. The sulfonated adduct is readily converted under basic conditions to yield uracil. Prior to such treatment, the ssDNA is also highly negatively charged, and is believed to have different solubility and binding properties. Accordingly, in some embodiments of the present size-exclusion purification methods, samples containing the 6-sulfonate adduct of uracil are treated with base to form uracil, and the resulting treated nucleic acid is sufficiently soluble in the buffer. After desulfonation, TE buffer can be used to collect the sample.

The examples described herein are certain embodiments chosen to illustrate the invention, and are not intended to be limiting. Rather, those reasonably skilled in the art will readily recognize additional embodiments that do not differ from the scope and spirit of the invention disclosed herein.

EXAMPLES

The nucleic acid samples for bisulfite treatment may be obtained by any conventional collection and purification process prior to use in the methods of the invention. The examples discussed below used commercially available sample lines (from Coriell or Intergen) of known methylation status, to assess the viability of the methods.

Each sample discussed herein was analyzed by methyl-specific PCR (MSP). MSP provides a relatively fast analysis method for methylation status of bisulfite-treated DNA samples, providing a yes/no answer. The method is based on using primer pair sets. One primer pair is designed to anneal/PCR amplify only if all cytosines were successfully converted to uracil, and the other primer pair in the set annealed/PCR amplified if the methylated cytosine (CpG cytosines only) were methylated, and therefore not converted to uracil.

The MSP pairs that amplify specific gene fragments, and the expected size of the amplicon, are the following:

for the p16 gene, unmethylated reaction (size 151):

```
5'-TTATTAGAGGGTGGGGTGGATTGT-3'    (SEQ ID NO:1)
                                  (sense), 5'-CAACCCCAAACCACAACCATAA-3'      (SEQ ID NO:2)
                                  (antisense);
``` methylated reaction (size 150):

```
5'-TTATTAGAGGGTGGGCGGATCGC-3'     (SEQ ID NO:3)
                                  (sense), 5'-GACCCCGAACCG-CGACCGTAA-3'      (SEQ ID NO:4)
                                  (antisense);
``` for the MGMT gene, unmethylated reaction (93):

```
5'-TTTGTGTTTTGATGTTTGTAGGTTTTTGT-3'  (SEQ ID NO:5)
                                     (sense), 5'-AACTCCACACTCTTCCAAAAACAAAACA-3'   (SEQ ID NO:6)
                                     (antisense);
``` methylated reaction (81):

```
5'-TTTCGACGTTCGTAGGTTTTCGC-3'     (SEQ ID NO:7)
                                  (sense), 5'-GCACTCTTCCGAAA-ACGAAACG-3'     (SEQ ID NO:8)
                                  (antisense);
``` for the DAP-kinase gene, unmethylated reaction:

```
5'-GGAGGATAGTTGGATTGAGTTAATGTT-3'  (SEQ ID NO:9)
                                   (sense), 5'-CAATCCCT-CCCAAACACCAA-3'        (SEQ ID NO:10)
                                   (antisense);
``` methylated reaction:

| | |
|---|---|
| 5'-GGATAGTCGGATCGAGTTAACGTC-3' | (SEQ ID NO:11) (sense), |
| 5'-CCCTCCCAAACGCCG-3' | (SEQ ID NO:12) (antisense); | for the MLH1 gene, unmethylated reaction (124):

| | |
|---|---|
| 5'- TTTTGATGTAGATGTTTTATTAGGGTTGT | (SEQ ID NO:13) (sense), |
| 5'- ACCACCTCATCATAACTACCCACA | (SEQ ID NO:14) (antisense); | methylated reaction (115)

| | |
|---|---|
| 5'- ACGTAGACGTTTTATTAGGGTCGC | (SEQ ID NO:15) (sense), |
| 5'- CCTCATCGTAACTACCCGCG | (SEQ ID NO:16) (antisense); | for the p15 gene, unmethylated reaction (154):

| | |
|---|---|
| 5'-TGTGATGTGTTTGTATTTTGTGGTT | (SEQ ID NO:17) (sense), |
| 5'-CCATACAATAACCAAACAACCAA | (SEQ ID NO:18) (antisense); | methylated reaction (148)

| | |
|---|---|
| 5'-GCGTTCGTATTTTGCGGTT | (SEQ ID NO:19) (sense), |
| 5'-CGTACAATAACCGAACGACCGA | (SEQ ID NO:20) (antisense). |

A PCR protocol used to evaluate samples was:

| | |
|---|---|
| 2X Taq Gold PCR Master Mix | 10 µL |
| Fwd primer (5 uM) | 1 µL |
| Rev primer (5 uM) | 1 µL |
| Bisulfite treated DNA | 0.5 µL |
| H2O | 7.5 µL |
| | 20 µL |

2x TaqGold PCR master mix is commercially available from Applied Biosystems. The forward and reverse primer sequences are those listed above. The bisulfite treated DNA, was obtained from the various bisulfite-conversion experiments described throughout the patent application.

The following thermal cycling schedule was used:

| | |
|---|---|
| 40 cycles | 95 deg 5 min |
| | 95 deg 30 sec |
| | 60 deg 45 sec |
| | 72 deg 1:00 min |
| | 4 deg forever |

One of the primers in each set was synthesized with a 5'FAM label. A 1 uL aliquot of the above PCR reaction was added to HiDi formamide with ROX 500 size standard added, and denatured by heating at 95° C. for 5 min. By using a FAM-labeled primer, the PCR amplicon was directly analyzed on an ABI PRISM® 310 Genetic Analyzer, with POP-4™ polymer, using run module "GS POP4 (1 mL) A" (reagents and instrument all from Applied Biosystems).

The presence of a PCR amplicon of the correct size seen in the 310 was evidence of a successful reaction. Additionally, the size of the peak (or area) could be used empirically to determine how much template (i.e. bisulfite-treated gDNA) was initially present. The bigger the peak, the more DNA was present initially.

The MSP-PCR product was then sometimes sequenced for further "resolution". DNA sequencing was by standard protocol and reagents from Applied Biosystems.

Prior to sequencing of the PCR amplicon, the primers and excess dNTPs used during the MSP-PCR were removed by treatment of a 4 µL aliquot of the PCR reaction with an equal volume mixture containing 2 Units each of Shrimp Alkaline Phosphatase (SAP) and exonuclease 1 (exo) (USB Corporation, Cleveland, Ohio). The reaction was incubated at 37° C. for 1 hr, and then heat-denatured at 75° C. for 15 min. A 4 µL aliquot of the exo/SAP reaction was added to a solution containing 1-4 µL of BigDye® Terminator v1.1 cycle sequencing reaction mix (Applied Biosystems), 2 µL of BigDye® Terminator v1.1 5× sequencing buffer, 2 µL of the reverse PCR primer (5 uM)(which did not have a FAM-label), and enough water for a final volume of 20 µL. Thermal cycling: 95° C./1 min, 50 cycles of 96° C./10 sec, 52 ° C./10 sec, 60° C./4 min, and stored at 4° C. The cycle-sequencing reaction products were purified by an Edge Biosystems Performa® 96-well plate, dried under vacuum, dissolved in 20 µL of HiDi Formamnide and analyzed on an ABI PRISM® 3730 DNA Analyzer with KB basecaller or a 3700 DNA Analyzer.

Comparison of Size Exclusion Purification Using Microcon Device With Commercially Available Protocol A commercially available kit for bisulfite-conversion of a gDNA sample was compared to the new size-exclusion method. The kit, EZ DNA Methylation Kit™ available from Zymo Research, has a standard sodium bisulfite conversion protocol and a standard clean-up procedure. The Zymo bisulfite protocol was followed exactly for 8 samples (i.e. 4 samples in duplicate), and reacted at 50° C. for each of a 6 hour reaction and a, recommended, 15 hour reaction. Thus, 16 samples in all were used for this experiment. In each case, 300 ng of gDNA was used in the bisulfite conversion step. The samples were Coriell #35, Coriell #13705, p16M (from Intergen's p16 kit), and Universally Methylated DNA (Intergen). One plate was reacted for 6 hours and the other for 15 hours, both at 50° C. For each plate, 4 samples were purified using the standard Zymo protocol and the remaining duplicate 4 samples were purified using the inventors' size-exclusion purification method.

Specifically, the Zymo purification protocol calls for adding and mixing 400 µL of their "M-Binding Buffer" to the DNA sample. The sample is then loaded into a "Zymo-Spin I Column" and placed into a 2 ml collection tube and centrifuged at full speed, >10,000 RPM, for 15–30 seconds. The flow-through is then removed. 200 µL M-Wash Buffer is added and the sample is spun again at full speed for 15–30 seconds. 200 µL M-Desulfonation Buffer is added and left to stand at room temperature for 15 minutes. The sample is then spun, again, at full speed for 15–30 seconds. Another 200 µL of the Wash Buffer is added and the sample spun at full speed for 15–30 seconds. An additional 200 µL of Wash Buffer is added and spun at full speed for 30 seconds. This spin was longer to complete removal of the wash buffer residues. Throughout the process, the flow-through is discarded as necessary to prevent contamination by reverse flow-through. Finally, 10 µL of M-Elution Buffer is added directly to the column matrix. The sample is spun in a 1.5 mL tube to elute the DNA, which is collected and ready for PCR. Zymo recommends 2–4 µL for each PCR reaction. In the experiment, 1.5 µL was used to conserve sample.

Alternatively, bisulfite-treated samples herein were treated according to the following steps a–h:

a. The sample was diluted with 200 µL water in a Microcon 100 device;

b. The sample was centrifuged at about 2800 RPM for about 8 minutes, the filtrate was removed;

c. 300 µL water was added to the device and centrifuged at about 2800 RPM for about 8 minutes, the filtrate was removed;

d. 300 µL water was added to the device and centrifuged at about 2800 RPM for about 8 minutes, the filtrate was removed;

e. 300 µL 0.1N NaOH was added to the device and centrifuged at about 2800 RPM for about 8 minutes, the filtrate was removed;

f. 300 µL water was added to the device and centrifuged at about 2800 RPM for about 6–8 minutes, the filtrate was removed;

g. 50 µL TE buffer was added to the top chamber and allowed to sit for 5 minutes;

h. The device was inverted, and the purified sample was collected for use in PCR.

Only water and a simple NaOH solution are required in addition to standard TE buffer solution in this embodiment. In step e, NaOH is added to facilitate in situ desulfonation, pushing the reaction towards completion yielding uracil from its 6-sulfonate adduct. Prior attempts to purify the sample by size-exclusion without the addition of NaOH were not successful.

Five primer pair sets, targeted for specific genes, were used to evaluate the success of the two purification protocols. The primers amplify only the bisulfite-converted DNA. The amount of amplicon (PCR product) was used to estimate the amount of DNA recovered from the purification step. Since each sample was bisulfite-converted identically, the comparison of the resultant quantity of PCR product was a direct comparison of the successful recovery of material from the purification. In all cases, microfiltration (also referred to as ultrafiltration)-based purification led to better and/or more successful amplicon formation than the purification process taught by the Zymo kit.

In some experiments, about 5 times or more of the Zymo-purified DNA sample was used in the PCR work-up when compared to the amount of the size-exclusion purified product. Despite this difference, microfiltration-purified samples still yielded bigger and stronger product peaks. For example, peaks obtained on an ABI 310 Genetic Analyzer for E2F2 template show little if any product peak for the Coriell #35 sample purified by the Zymo protocol, while a much stronger product peak results for the same sample purified by size-exclusion. Similar comparisons can be made with other samples. These results were confirmed subsequently by SYBR green assay. Thus, a recovery at least five-fold that of the Zymo purification was obtained.

In a further study involving serial dilutions of the amount of gDNA treated by the Zymo bisulfite kit and purified according to the size-exclusion methods described herein, it was found that as little as 0.3 ng (300 picograms) can be bisulfite-converted, and that 1/10 of the final Microcon recovered product (30 pg) can be used successfully in PCR. For the 300 and 30 ng examples, 50 µL of TE was used for the recovery of the purified bisulfite-treated DNA from the Microcon 100. For the 3 ng and 0.3 ng samples, only 10 µL TE was used. In all cases, 1 µL of the TE solution was used in PCR. PCR amplicon was seen for 8 different PCR experiments at all dilutions except for some of the most dilute. However, most of even the diluted samples (30 pg) still yielded PCR product at least 50% of the time.

Further Comparisons With Other Devices

Further studies were undertaken using different sizes and brands of size exclusion devices. A 300 k device, Nanosep 300, did not trap the bisulfite-treated DNA, possibly due to the DNA either being trapped in the (more) porous membrane, or because the DNA had been fragmented during the bisulfite treatment into pieces less than 300K. 100K devices such as Nanosep 100, and Microcon 100 were successful, as were 30K devices (Microcon 30). 10K devices (Microcon 10) were not suitable for use due to the high salt content required in the bisulfite conversion reaction; the centrifugation times required in the 10K devices were very long. From these studies, it was concluded that at least devices having 100K, and 30K cut offs are useful in the various embodiments of the methods disclosed herein, although those of skill in the art will appreciate that because filtration materials in the size exclusion devices may vary, for example by brand and/or materials, cut-off values alone, while indicative, are not determinative of which devices can function in the presently disclosed methods.

Filtration materials within the device vary by brand. Microcon uses modified cellulose, while Nanosep uses a "modified polyethersulfone on polyethylene substrate." A comparison of samples prepared with the Zymo kit and purified by either Nanosep 100 or Microcon 100 indicate that although the Microcon 100 appeared to give better results, the Microcon 100, and Nanosep 100 all achieve substantially similar results when centrifugation speeds of about 2800 RPM are not exceeded. All experiments below were conducted with a Microcon 100 unless indicated otherwise.

Applicability to Magnesium Bisulfite and Catalyzed Conversion Protocols

The present methods are also applicable to magnesium bisulfite and/or amine/quaternary amine catalyzed conversion protocols, and provide good results and quicker analyses without the use of overnight precipitation steps found in some prior methods. This enables the more rapid assessment of the conversion reactions, and also increase yields.

In such protocols, the sodium bisulfite can be replaced with magnesium bisulfite and a catalyst as described in the contemporaneously filed application entitled "Method And Materials For Quaternary Amine Catalyzed Bisulfite Conversion Of Cytosine To Uracil" described above.

Effect of Antioxidant and Concentration of Quaternary Amine

Examples 1–4, shown below in Table 1, vary with respect to presence of antioxidant and amount of quaternary amine.

TABLE 1

| Ex. 1 | Ex. 2 | Ex. 3 | Ex. 4 |
| --- | --- | --- | --- |
| 3 µL NA 13705 | 3 µL NA 13705 | 3 µL NA 13705 | 3 µL NA 13705 |
| 5.5 µL 2 M NaOH | 5.5 µL 2 M NaOH | 35 µL water | 35 µL water |
| 45 µL 2 M TBAC | 45 µL 2 M TBAC | 10 µL 20% Et$_4$NOH | 20 µL 20% Et$_4$NOH |
| incubate at 37° for 10–12 minutes | incubate at 37° for 10–12 minutes | | |
| 55 µL 2 M Mg(HSO$_3$)$_2$ | 30 µL Hydroquinone | 85 µL 2 M Mg(HSO$_3$)$_2$ | 60 µL 2 M Mg(HSO$_3$)$_2$ |
| — | 85 µL 2 M Mg(HSO$_3$)$_2$ | — | — |

Each of the reactions in Examples 1–4 were incubated at 50° for four hours. The reaction mixture in Example 4 immediately formed a large amount of precipitate, which remained even after incubation, and was excluded from further study. Example 3 had a non-interfering amount of precipitate and was retained in the study. After the four hour incubation, the remaining three samples were purified using a size-exclusion purification process, in this case, a Microcon 100 (Millipore) size-exclusion device. The sample and 200 μL of water were added to the Microcon 100 device, and the sample was then spun in the device at approximately 2800 RPM for about 8 minutes (as per manufacturers recommendation). The resultant filtrate was removed. Two subsequent washes with about 300 μL water, each spun at about 2800 RPM for 8 minutes followed. After each, the filtrate was again removed. About 300 μL 0.1N NaOH was added and spun at approximately 2800 RPM for about 8 minutes. Again, the filtrate was removed. After addition of about 300 μL of water, the sample was spun in the device at 2800 RPM for about 6–8 minutes. The filtrate was removed and about 50 μL TE buffer was added. After about 5 minutes before it was inverted to collect the purified DNA sample in a centrifuge. Approximately 60 μL were collected.

The bisulfite-treated DNA was analyzed by MSP using the following MSP primer sets: p15 M, p15 U, Dapk M, Dapk U, Mgmt M, Mgmt U, p16 M, and p16 U. Hydroquinone did not appear to greatly enhance PCR yields. The $Et_4NOH$ sample displayed a far greater product peak than TBAC with or without hydroquinone. Only about 6 ng of bisulfite-treated gDNA was used per PCR. Prior experiments using the published purification protocol (Wizard resin) provided much less isolated DNA based on the amount required for successful PCR. These data support the use of quaternary amine, and specifically $Et_4NOH$, as a catalyst.

Reduced gDNA Concentration in $Et_4NOH$ Catalyzed Magnesium Bisulfite Reaction

The samples in Examples 5–8, shown in Table 2, demonstrate the bisulfite conversion of reduced amounts of DNA. These samples vary with respect to either the amount of DNA used, or reduced concentration of magnesium bisulfite/$Et_4NOH$.

TABLE 2

| Ex. 5 | Ex. 6 | Ex. 7 | Ex. 8 |
|---|---|---|---|
| 3 μL Coriell 13705 | 1 μL Coriell 13705 | 1 μL Coriell 13705 | 1 μL Coriell 13705 |
| 35 μL water | 35 μL water | 35 μL water | 35 μL water |
| 10 μL 20% $Et_4NOH$ | 10 μL 20% $Et_4NOH$ | 5 μL 20% $Et_4NOH$ | 2.5 μL 20% $Et_4NOH$ |
| 85 μL 2 M $Mg(HSO_3)_2$ | 85 μL 2 M $Mg(HSO_3)_2$ | 40 μL 2 M $Mg(HSO_3)_2$ | 85 μL 2 M $Mg(HSO_3)_2$ |
| ~1.3 M final | ~1.3 M final | ~1.0 M final | ~0.8 M final |

The reaction in Example 5 (3 μL of Coriell) contained about 1 μg DNA, and Examples 6–8 (1 μL of Coriell) contains about 300 ng DNA. Each of these samples was allowed to react as previously discussed, at 50° C. for four hours. Subsequent to this incubation period, each was subject to the size-exclusion purification process discussed above, using the Microcon 100 device. The process differed from that previously discussed only in that slightly more water was used, and about 350 μL of 0.1M NaOH was used. Each was collected in about 50 μL TE buffer, and 1 μL was used in subsequent PCR. Surprisingly, the 300 ng sample at 1.3M magnesium bisulfite (Example 6) was observed to provide more PCR product than the 1 μg sample (Example 5).

At lower bisulfite concentration (0.8 and 1.0M) bisulfite conversion was apparently incomplete (Ex. 6–8). Accordingly, it may be desirable to vary reaction conditions to optimize reaction yields.

Effect of Enzyme Concentration and Template (gDNA) Concentration in MSP

The same bisulfite-treated samples above, specifically, Ex. 5 and Ex. 6, were further analyzed by MSP under alternative conditions: (a) additional polymerase (TaqGold) and (b) less bisulfite-treated gDNA template. The MSP conditions are shown in Table 3, below.

TABLE 3

| Ex. 9 | Ex. 10 | Ex. 11 | Ex. 12 | Ex. 13 | Ex. 14 |
|---|---|---|---|---|---|
| Ex. 5 bisulfite-treated DNA with xs enzyme | Ex. 6 bisulfite-treated DNA with xs enzyme | NTC with xs enzyme | 1/10 of Ex. 5 bisulfite-treated DNA (0.6 ng/μL) | 1/20 of Ex. 5 bisulfite-treated DNA (0.3 ng/μL) | 1/30 of Ex. 5 bisulfite-treated DNA (0.2 ng/μL) |

Each PCR was prepared as described in the MSP analysis described elsewhere herein. MSP primer sets used were Mlh M, Mlh U, Dapk M, Dapk U, Mgmt M, Mgmt U, p16 M, and p16 U. When excess TaqGold polymerase was used, an additional 2 μL (2 units) was added to the reaction.

The results show that extra enzyme in the Master Mix forced "mispriming" to occur (determined by subsequent sequencing). The 1/10, 1/20, and 1/30 dilutions of the Microcon 100 purified bisulfite-treated gDNA still provided enough gDNA template for MSP for almost all of the reactions. Successful PCR was seen even when only 0.2 ng of gDNA was used in MSP. Although there were two data points that "dropped out," overall the data are excellent. Thus, it appears that as little as 0.2 ng of DNA can provide good PCR yields.

Studies Using Additional Templates

The following experiments include side by side comparison of methylated to unmethylated gDNA. Five additional "control" reactions were evaluated with both methylated and unmethylated gDNA. These samples contained 1 μL DNA from Coriell or 3 μL DNA from the Intergen p16 kit (each about 300 ng DNA), 35 μL water, 10 μL 20% $Et_4NOH$, and 85 μL 2M magnesium bisulfite and heated at 50° C. for about 4 hours. The samples were Coriell #34 and #35, and DNA from Intergen's p16 "kit," p16U, p16M, and a universally methylated gDNA. Each was incubated at 50° for four hours and subjected to the size-exclusion clean-up method, using a Microcon 100 filtration unit received 50 mL TE. One mL was used in MSP with the following MSP primer pairs:

MLH M, MLH U, Dapk M, Dapk U, Mgmt M, Mgmt U, p16M, and p16 U. Excellent MSP yields were obtained as evidence by an amplicon of the correct size, several of the PCRs were subjected to direct sequencing.

Comparison of Magnesium Bisulfite/Et$_4$NOH to Sodium Bisulfite Protocol After 6 Hour and 15 Hour Reaction Times A direct comparison between samples prepared according to the sodium bisulfite protocol of J. Herman, *Proc. Natl. Acad. Sci.* 93, 9821–26 (1996) and the magnesium bisulfite protocol as described above in Ex. 10 was conducted, using Et$_4$NOH, NaOH, and no additive. Two plates were set up, one for a 6 hour analysis and the other for a 15 hour analysis. Both reactions took place at 50° C. Only an unmethylated gDNA sample was investigated. All reaction products were purified by the size-exclusion clean-up procedure described above and recovered in a final volume of 50 μL of TE MSP was used to analyze the converted DNA. The sodium bisulfite procedure provided gDNA that gave excellent results in MSP. The magnesium bisulfite converted gDNA gave much weaker signals in MSP than the sodium bisulfite converted DNA. However, the magnesium bisulfite/Et$_4$NOH differs from the sodium bisulfite protocol in significant ways. The magnesium bisulfite/Et$_4$NOH was achieved without a pre-denaturation step, e.g., with a much lower concentration of bisulfite, no exacting pH control, no antioxidant, and reagents were "off the shelf" and not freshly prepared.

The size-exclusion purification worked well on the sodium bisulfite samples as well as the magnesium bisulfite samples.

Direct Comparison of Magnesium Bisulfite with Et$_4$NOH and Sodium Bisulfite Reactions on Both Methylated and Unmethylated gDNA The 1.3M (final concentration) magnesium bisulfite with Et$_4$NOH reaction was compared to the samples treated with sodium bisulfate, according to the known method. The magnesium bisulfite recipe was 1 μL Coriell or 3 μL Intergen, 32 or 34 μL water, 10 μL 20% Et$_4$NOH, 85 μL 2M magnesium bisulfite. Two methylated samples and two unmethylated samples were compared in side by side reactions with sodium bisulfite and the magnesium bisulfite. These were allowed to react for 6 and 15 hours at 50° C for a total of sixteen (16) samples processed. Purification by the size-exclusion process described above was performed. In this very thorough comparison, the 16 samples, purified by Microcon 100, were all analyzed by sequencing. (The sequencing analysis allows for all cytosine in a given region to be analyzed for completeness of the bisulfite conversion to uracil.).

Eleven different primer sets for specific gene targets were used: E2F2, FRAP, XPD, CDKN, RalDGS, IDT, CDH1, APC1, and ESR.

Evaluation with Known Tumor Suppressor Gene Targets

DNA was purchased from the Coriell cell repository (http://locus.umdnj.edu/nigms/pdr.html). Universally methylated DNA was purchased from Serologicals (Norcross, Ga.). Three hundred nanograms of purified DNA were bisulfite treated in accordance with J. Herman, *Proc. Natl. Acad. Sci.* 93, 9821–26 (1996) with the following modifications. The reaction was scaled so that the final volume was 200 μL and was incubated in a microfuge tube in a thermal cycler without mineral oil. Alternatively, bisulfite conversion was investigated using reagents supplied by Zymo Research (Orange, Calif.) and the manufacturer's recommended protocol, but only for the bisulfite treatment and not using the purification cartridge supplied with the Zymo kit. Instead, after 15 hrs incubation in bisulfite solution at 50° C., the Zymo treated samples and the samples prepared according to Herman were purified by Applicants' size-exclusion method. The bisulfite-DNA was purified by the following steps:

1. Dilute a bisulfite reaction with water so that the total volume is 350–450 μL.
2. Transfer solution to an assembled Microcon 100 device (Millipore).
3. Centrifuge at 2800 rpm (Eppendorf 5414) for 8–10 min 500×g maximum, according to manufacturer.
4. Discard filtrate, add 350 μL of water to the upper chamber and centrifuge 6–8 min at 2800 rpm.
5. Discard filtrate, add 350 μL of water to the upper chamber and centrifuge 6–8 min at 2800 rpm.
6. Discard filtrate, add 350 μL of 0.1M NaOH (sodium hydroxide) to the upper chamber and centrifuge at 2800 rpm for 6 min (In situ desulfonation).
7. Discard filtrate, add 350 μL of water to the upper chamber and centrifuge at 2800 rpm for 6–8 minutes, leaving slightly damp/small amount of liquid in the upper chamber.
8. Elute sample by adding 50 μL of 1× TE buffer, pipet up and down several times to mix, and let stand in column for 5 min.
9. Invert device and collect TE solution of the bisulfite-treated DNA in a clean, labeled Eppendorf tube.

The collected sample was then subjected to PCR. Typically, 0.5 μL (approx. 3 ng, if 100% yield) of the bisulfite-converted DNA was used in a 20 μL PCR reaction prepared with 2× AmpliTaq Gold® PCR Master Mix (Applied Biosystems, Foster City, Calif.) and containing 250 nM each of the forward and reverse primer. Thermal cycling: 5 min at 95° C., 40 cycles of 95° C./30 sec, 60° C./45 sec, 72° C./1 min, and stored at 4° C. By using a FAM-labled primer, the PCR amplicon was directly analyzed on an ABI PRISM® 310 Genetic Analyzer, with POP-4™ polymer, using run module "GS POP4 (1 mL) A".

Prior to sequencing of the PCR amplicon, the primers and excess dNTPs were removed by treatment of a 4 μL aliquot of the PCR reaction with an equal volume mixture containing 2 Units each of Shrimp Alkaline Phosphatase (SAP) and exonuclease 1 (exo) (USB Corporation, Cleveland, Ohio). The reaction was incubated at 37° C. for 1 hr, and then heat-denatured at 75° C. for 15 min. A 4 μL aliquot of the exo/SAP reaction was added to a solution containing 1–4 μL of BigDye® Terminator v1.1 cycle sequencing reaction mix (Applied Biosystems), 2 μL of BigDye® Terminator v1.1 5× sequencing buffer, 2 μL of the reverse PCR primer (5 uM), and enough water for a final volume of 20 μL. Thermal cycling: 95° C./1 min, 50 cycles of 96° C./10 sec, 52° C./10 sec, 60°0 C./4 min, and stored at 4° C. The cycle-sequencing reaction products were purified by an Edge Performa 96-well plate, dried under vacuum, dissolved in 20 μL of HiDi Formamide and analyzed on an ABI Prism 3730 DNA Analyzer with KB basecaller or a 3700 DNA Analyzer.

Primers were designed to contain no CpG in the sequence so that both the methylated and unmethylated samples would produce an amplicon with one primer pair. The primers were often automatically selected by use of the website: "http://itsa.ucsf.edu/~urolab/methprimer/". By cutting and pasting in a section of a genomic sequence of interest, the software program converts C to T, flags the CpG's and recommends forward and reverse primers that meet the program's criteria.

A number of previously reported tumor suppressor gene targets (18) that reportedly show a correlation in methylation status and gene expression (or cancer) were sequenced (data not presented) to validate the bisulfite sequencing protocol described herein, using a fully-methylated "control" and a sample obtained from the Coriell cell repository. Cytosine was only seen in CpGs that were methylated. The immortalized cells obtained from Coriell were unmethylated in most regions, but methylated (at CpGs) in some regions. All Coriell samples sequenced, if methylated, were methylated in the same region.

A total of 25 gene targets were investigated, and successfully sequenced, providing that amplicons containing greater than 9 sequential T's were avoided. Multiple T's in the PCR amplicon caused "slippage", which was observed in the sequencing trace as the N+1 and/or N−1 sequence superimposed on the correct sequence. Simple changes to primer design can be made to avoid amplicons having 9 or more T's, thereby reducing slippage. Generally, slippage did not impair the ability to correctly determine the sequence.

The methods disclosed herein are viable alternatives to the sodium bisulfite reaction. The studies herein utilized 2M magnesium bisulfite solution, which is diluted in the sample to about 1.3M. Use of a more concentrated magnesium bisulfite solution would yield higher bisulfite concentration for conversion, while still keeping reaction volumes to a minimum. Such increased bisulfite concentration in the reaction mixture could easily be employed, and would be expected to enhance PCR yields. The optimization of such reaction parameters, including volume and/or concentration of magnesium bisulfite solution, temperature, pH and other reaction conditions are expected to lead to more complete conversion, and are well within the skill of the art.

Size-exclusion purification processes described herein can provide bigger, stronger product peaks, with shorter reaction times and easier clean-up methods.

While the above-described methods of PCR and sequencing are currently preferred for use with the purification methods described herein, they are not the only methods useable. The present invention is not limited to these any particular embodiments, or any of the examples above. Rather, other variants of these methods will be apparent to those skilled in the art and are within the scope and spirit of the invention disclosed herein.

What is claimed is:

1. A method for the purification of a bisulfite-treated nucleic acid comprising the steps of:
   (a) providing a liquid comprising a bisulfite-treated nucleic acid in a size-exclusion device comprising a porous, size-discriminating barrier;
   (b) washing said nucleic acid in said size-exclusion device by passing liquid through said barrier while said imcleic acid is retained by said barrier;
   (c) treating said washed nucleic acid with a base in said size-exclusion device to increase the pH; and
   (d) optionally washing said nucleic acid resulting from step (c), resulting in a purified bisulfite-treated nucleic acid.

2. The method of claim 1 wherein said step (d) is performed in said size-exclusion device.

3. The method of claim 1 wherein said porous, size-discriminating barrier has a 300K cut off.

4. The method of claim 1 wherein said porous, size-discriminating barrier has a 30K cut off.

5. The method of claim 1 wherein said porous, size-discriminating barrier has a 100K cut off.

6. A method of converting one or more cytosine bases to uracil bases in a nucleic acid, the method comprising:
   contacting the nucleic acid with a bisulfite conversion reagent, thereby forming a bisulfite-treated nucleic acid,
   washing the treated nucleic acid in a size-exclusion device comprising a porous, size-discriminating barrier that allows residual bisulfite conversion reagent to pass through while retaining the bisulfitetreated nucleic acid, and
   subjecting the retained bisulfite-treated nucleic acid to basic conditions comprising a pH of 10 or above, during or after said washing, to form a nucleic acid in which at least one cytosine base has been converted to a uracil base.

7. The method of claim 6 wherein the porous, size-discrimination barrier comprises a membrane.

8. The method of claim 6 wherein said barrier has a 300K cut off.

9. The method of claim 6 wherein said barrier has a 100K cut off.

10. The method of claim 6 wherein said barrier has a 30K cut off.

11. The method of claim 6 wherein said washing is performed under pressure.

12. The method of claim 6 wherein said washing comprises centrifugation of the device.

13. The method of claim 6 wherein said bisulfite conversion reagent comprises sodium bisulfite.

14. The method of claim 6 wherein said bisulfite conversion reagent comprises magnesium bisulfite.

15. The method of claim 6 wherein said basic conditions comprise 0.1M NaOH.

* * * * *